US010295173B1

(12) United States Patent
Most et al.

(10) Patent No.: US 10,295,173 B1
(45) Date of Patent: May 21, 2019

(54) IMPLEMENTATION OF AEROGEL INSULATION IN A PORTABLE VAPORIZER

(71) Applicants: Matthew Isaac Most, Boulder, CO (US); Trevor Glen Vita, Boulder, CO (US)

(72) Inventors: Matthew Isaac Most, Boulder, CO (US); Trevor Glen Vita, Boulder, CO (US)

( * ) Notice: Subject to any disclaimer, the term of this patent is extended or adjusted under 35 U.S.C. 154(b) by 615 days.

(21) Appl. No.: 14/960,112

(22) Filed: Dec. 4, 2015

Related U.S. Application Data

(60) Provisional application No. 62/088,048, filed on Dec. 5, 2014, provisional application No. 62/087,751, filed on Dec. 4, 2014, provisional application No. 62/087,749, filed on Dec. 4, 2014, provisional application No. 62/087,747, filed on Dec. 4, 2014.

(51) Int. Cl.
*A61M 16/14* (2006.01)
*F22B 1/28* (2006.01)
*B23P 15/00* (2006.01)

(52) U.S. Cl.
CPC ............ *F22B 1/28* (2013.01); *B23P 15/00* (2013.01)

(58) Field of Classification Search
CPC .......... F22B 1/28; B23P 15/00; A61M 15/06; A61M 11/042; A61M 15/0023; A61M 15/0025; A61M 11/041; A61M 11/00; A61M 15/0026; A61M 2205/3368; A61M 2205/581; A61M 2205/582; A61M 2205/8206; A61M 2205/8237; A61M 2209/084; A61M 2205/332; A61M 11/007; A61M 15/00; A61M 2016/024; G05B 11/36; A24F 47/008; G08B 5/36; H05B 1/0244; H05B 2203/021; G06F 3/02; F04C 2270/041
USPC ...................................... 392/386; 128/203.27
See application file for complete search history.

(56) References Cited

U.S. PATENT DOCUMENTS

| | | | | |
|---|---|---|---|---|
| 4,429,703 A | * | 2/1984 | Haber | A24F 47/002 131/273 |
| 5,306,555 A | * | 4/1994 | Ramamurthi | C01B 33/1585 428/292.1 |
| 5,869,545 A | * | 2/1999 | Biesmans | C08G 18/092 521/117 |
| 5,942,553 A | * | 8/1999 | Biesmans | C08G 18/022 252/62 |
| 7,651,773 B2 | * | 1/2010 | Larouche | B82Y 30/00 423/447.1 |
| 8,550,068 B2 | * | 10/2013 | Terry | A24F 47/008 128/200.12 |
| 9,022,026 B2 | * | 5/2015 | Fang | A24F 47/008 128/202.21 |
| 9,204,670 B2 | * | 12/2015 | Liu | A24F 47/008 |
| 9,259,035 B2 | * | 2/2016 | Terry | A24F 47/008 |
| 9,271,527 B2 | * | 3/2016 | Liu | A24F 47/002 |

(Continued)

*Primary Examiner* — Eric S Stapleton
(74) *Attorney, Agent, or Firm* — Marsh Fischmann & Breyfogle LLP; Russell T. Manning

(57) ABSTRACT

Disclosed herein is a portable herbal vaporizer having an outward appearance of a fountain pen. The vaporizer includes a vaporization chamber subjected to high temperatures. The vaporizer utilizes compacted particulate aerogel insulation to reduce heat loss while also providing a compact exterior package. The aerogel particles are contained in a sealed cavity, with is filled during manufacture by means of a centrifuge.

6 Claims, 8 Drawing Sheets

(56) References Cited

U.S. PATENT DOCUMENTS

| | | | | |
|---|---|---|---|---|
| 2001/0012819 A1* | 8/2001 | Sun | B01J 21/10 | 502/237 |
| 2001/0050218 A1* | 12/2001 | Tabatabaie-Raissi | B01D 53/885 | 204/157.15 |
| 2003/0134161 A1* | 7/2003 | Gore | B65D 79/02 | 429/421 |
| 2006/0216602 A1* | 9/2006 | Larouche | B82Y 30/00 | 429/231.8 |
| 2007/0120095 A1* | 5/2007 | Gruner | B82Y 10/00 | 252/500 |
| 2007/0275177 A1* | 11/2007 | Mack | B28B 1/38 | 427/430.1 |
| 2008/0092912 A1* | 4/2008 | Robinson | A24F 47/008 | 131/200 |
| 2008/0188575 A1* | 8/2008 | Gaspar Martinho | B01J 13/0091 | 516/111 |
| 2010/0044230 A1* | 2/2010 | Papadimitrakopoulos | B01D 15/08 | 204/547 |
| 2010/0264048 A1* | 10/2010 | Gunsberg | A45C 15/00 | 206/314 |
| 2011/0126848 A1* | 6/2011 | Zuber | A24F 47/008 | 131/329 |
| 2012/0304990 A1* | 12/2012 | Todd | A61M 11/042 | 128/203.14 |
| 2012/0309245 A1* | 12/2012 | Liao | C08J 9/28 | 442/164 |
| 2013/0042865 A1* | 2/2013 | Monsees | A61M 15/06 | 128/203.27 |
| 2013/0108702 A1* | 5/2013 | Santra | A01N 59/20 | 424/490 |
| 2013/0152922 A1* | 6/2013 | Benassayag | A61M 15/06 | 128/202.21 |
| 2013/0276799 A1* | 10/2013 | Davidson | A24F 47/004 | 131/273 |
| 2013/0287661 A1* | 10/2013 | Begag | B01J 20/3085 | 423/228 |
| 2013/0312742 A1* | 11/2013 | Monsees | A61M 15/06 | 128/202.21 |
| 2014/0000638 A1* | 1/2014 | Sebastian | A24F 47/008 | 131/328 |
| 2014/0041655 A1* | 2/2014 | Barron | A61M 11/042 | 128/202.21 |
| 2014/0060556 A1* | 3/2014 | Liu | A24F 47/008 | 131/329 |
| 2014/0273701 A1* | 9/2014 | Samanta | E04B 1/78 | 442/334 |
| 2015/0173124 A1* | 6/2015 | Qiu | A24F 47/008 | 131/328 |
| 2016/0089508 A1* | 3/2016 | Smith | A61M 15/06 | 128/200.16 |

\* cited by examiner

```
┌─────────────────────────────┐
│   Attach aerogel well to    │
│      centrifuge device      │
│             302             │
└─────────────────────────────┘
              │
┌─────────────────────────────┐
│ Attach element with internal cavity to │
│ centrifuge outward of aerogel well │
│             304             │
└─────────────────────────────┘
              │
┌─────────────────────────────┐
│   Fluidly connect internal cavity of   │
│  element with interior of aerogel well │
│             306             │
└─────────────────────────────┘
              │
┌─────────────────────────────┐
│   Rotate aerogel well and attached   │
│ element to migrate aerogel into cavity │
│             308             │
└─────────────────────────────┘
```

IMPLEMENTATION OF AEROGEL INSULATION IN A PORTABLE VAPORIZER

CROSS-REFERENCE

The current application claims the benefit of the filing date of U.S. Provisional Application No. 62/087,751 having a filing date of Dec. 4, 2014, the entire contents of which is incorporated herein by reference.

FIELD

The present disclosure relates generally to filling at least partially enclosed cavities or chambers with an Aerogel insulation. In one, non-limiting, application, the present disclosure relates to inserting Aerogel insulation into a hollow wall cavity of a portable herb vaporizer.

BACKGROUND

In a number of applications, individuals extract the active ingredients of plant materials such as tobacco, herbs, oil and other beneficial materials (hereafter 'herbs') to treat a variety of conditions. Typically, the extracted ingredients are then delivered via inhalation to the individual. A vaporizer is a device used to extract the active ingredients of herbs for inhalation. Vaporization involves heating a material so that its active compounds boil off into a vapor. As opposed to smoking, i.e., burning, vaporization avoids the production of irritating, toxic, and carcinogenic by-products as no combustion occurs.

Vaporizers sometimes utilize a convection type heating element to heat air to a temperature sufficient to extract an herb's active ingredients. To remove an herb's active ingredients, the necessary air temperatures generally ranges from about 275 to 400 degrees Fahrenheit. The temperature varies depending on the type of herb to be vaporized.

User of vaporizers often prefer the devices to be small and portable. In this regard, users tend to prefer vaporizers having a small form factor similar in size to a pen or electronic cigarette. Further, the recent proliferation of high-power density batteries (e.g., lithium ion) has facilitated producing such small form factor/compact vaporizers. However, due to the high-temperatures required for vaporization, substantial thermal insulation is required to prevent the exterior of the device from reaching unsafe temperatures. That is, insulation between the heated air and the exterior of the device is required. However, such insulation can increases the minimum size of the device, as a thick thermal barrier may be required to create a necessary temperature gradient.

SUMMARY

Presented herein is an apparatus and a process. The apparatus is directed generally to an element having an internal cavity that is filled with an aerogel material. The process is directed to filling internal cavities with an aerogel material.

According to a first aspect, an electronics device is provided having a high temperature heat source and a high performance insulator at least partially surrounding the heat source. The heat source is disposed at least partially within the device and is at least partially surrounded by a housing. The housing may include an internal housing and external housing with a void or cavity there between. The cavity of the housing is filled with an aerogel material. More specifically, the aerogel material is a particulate material. Importantly, the particulate aerogel material is compacted in comparison to its loose form. In one arraignment, the particulate aerogel material has a compaction of 2:1 in relation to loose aerogel particles. In further arrangements, the aerogel material has a compaction of 4:1, 6:1 or even 8:1. In one particular application, the portable electronic device is an herbal vaporizer that houses a heating element for vaporizing herbs. An aerogel insulated housing surrounds the heating element and an herb chamber to minimize heat loss and reduce external temperatures of the device while permitting a compact exterior package.

In another aspect, a method for filling a cavity with compacted aerogel particles is provided. The method includes collectively centrifuging an aerogel supply (e.g., well) that is in fluid communication with an element having a cavity (e.g., close ended cavity) to be filled with aerogel material. The element is mounted more distally to a rotational axis of the centrifuge to allow aerogel particles to migrate outward into the cavity during rotation. The aerogel well and element are rotated at high relative centrifugal forces (e.g., RCF or G-forces) to both migrate and compact the aerogel particles in the cavity. In one arrangement, RCF forces exceed 1000, in another arrangement, RCF forces exceed 1250. In a further arrangement RCF forces exceed 3000. The result is that the aerogel particles are compacted 2-8 times in comparison with loose aerogel particles.

BRIEF DESCRIPTION OF THE DRAWINGS

FIG. 5 is a flow diagram illustrating a method for filling a close-ended cavity with aerogel particles using a centrifuge.

DETAILED DESCRIPTION

Reference will now be made to the accompanying drawings, which at least assist in illustrating the various pertinent features of the presented inventions. The following description is presented for purposes of illustration and description and is not intended to limit the inventions to the forms disclosed herein. Consequently, variations and modifications commensurate with the following teachings, and skill and knowledge of the relevant art, are within the scope of the presented inventions. The embodiments described herein are further intended to explain the best modes known of practicing the inventions and to enable others skilled in the art to utilize the inventions in such, or other embodiments and with various modifications required by the particular application(s) or use(s) of the presented inventions.

Figure 1A:
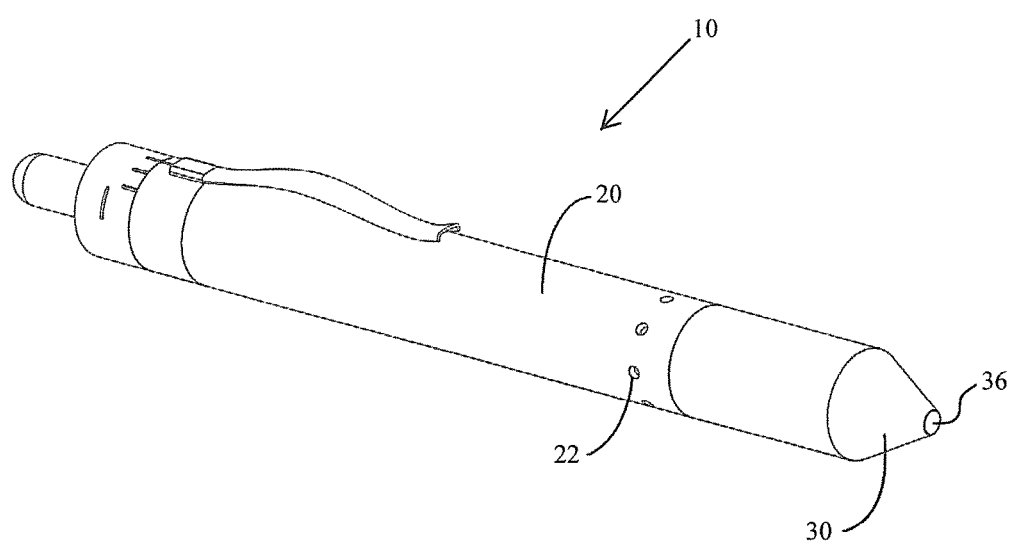
FIG. 1A is a perspective view of one embodiment of a vaporizer.

FIG. 1A illustrates a perspective view of a portable vaporizer 10 for extracting active ingredients of herbs for inhalation. The vaporizer 10 is similar in size and form to a fountain pen. As shown, the vaporizer 10 includes a cylindrical body 20 and a mouthpiece 30. The mouthpiece 30 tapers to an opening 36 that a user utilizes to draw air into the vaporizer via air inlet apertures 22 in the cylindrical body 10. More specifically, the air is drawn through the interior of the vaporizer 10 where it passes through an internal heating element/heating exchanger, which heats the air to a desired temperature. The heated air passes through an internal herb chamber which holds a supply of herbs, which may be at least partially vaporized. The user draws the resulting vapor through the opening 36 in the mouth piece.

Figure 1B:
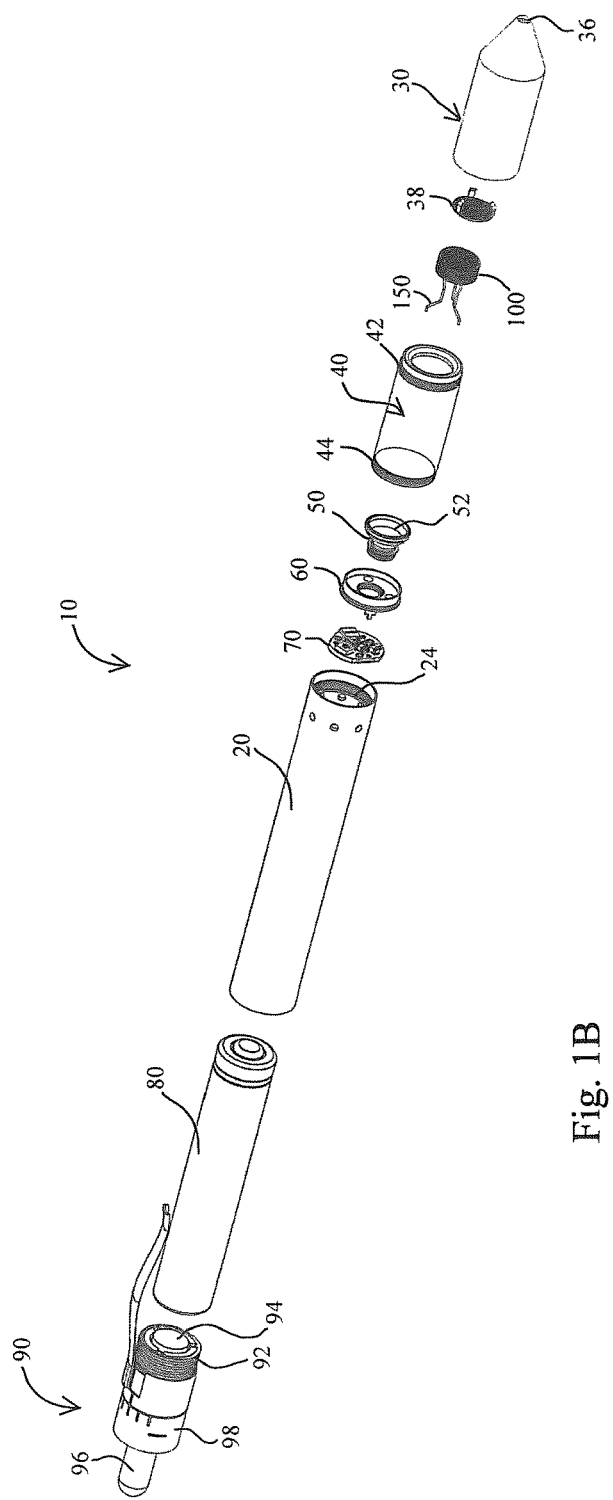
FIG. 1B is an exploded perspective view of the vaporizer of FIG. 1A.
Figure 1C:
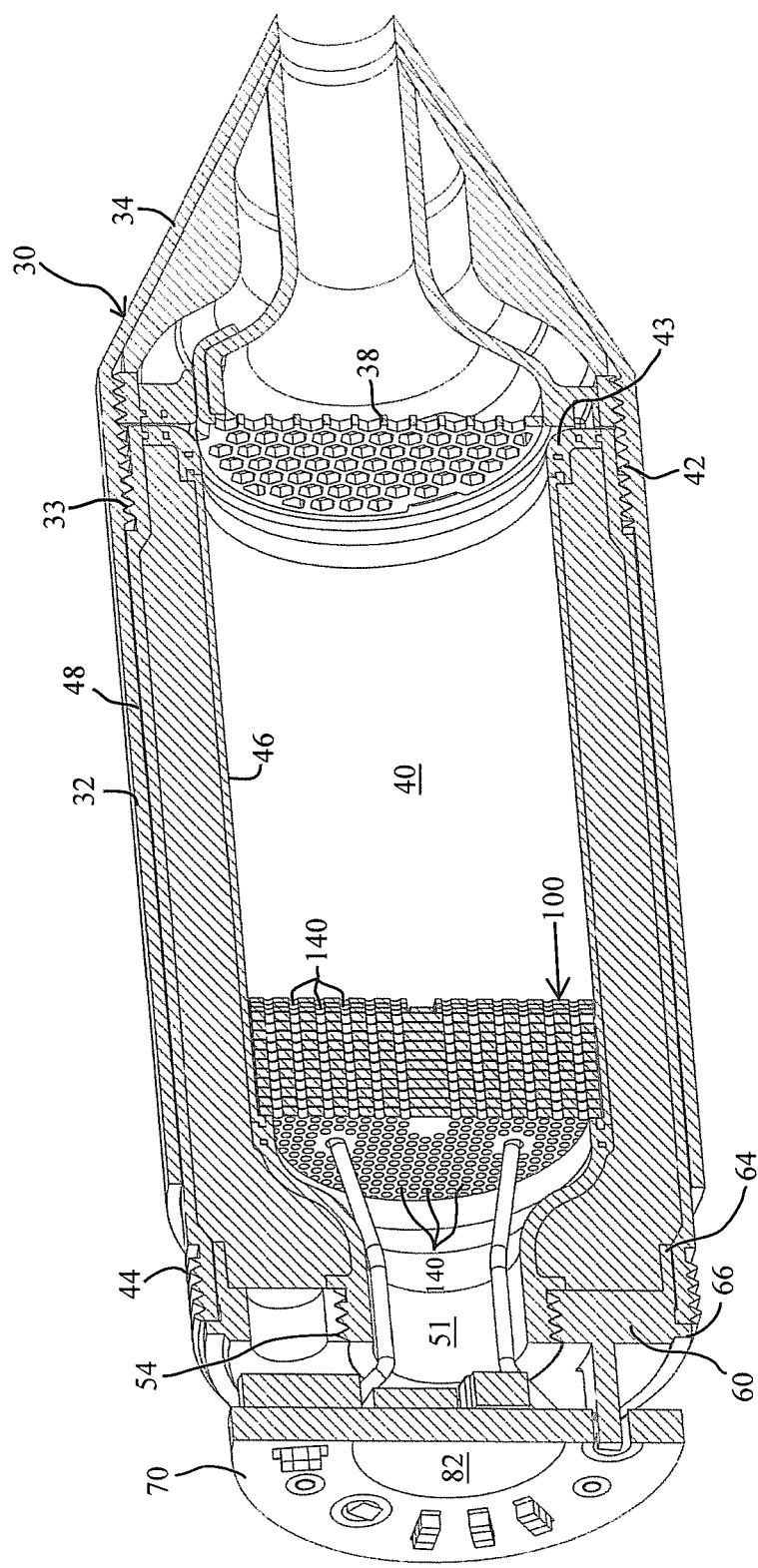
FIG. 1C is cross-sectional perspective view of a forward portion of the vaporizer of FIG. 1A.

FIG. 1B illustrates an exploded perspective view of the vaporizer 10 and FIG. 1C illustrates a cross-sectional view of an assembled forward portion of the vaporizer 10. As shown, the mouthpiece 30 is formed of a generally hollow cylindrical section 32 attached to a conical end section 34. The mouthpiece 30 includes internal threads 33 located near the transition between the cylindrical section 32 and the conical end section 34 as best shown in FIG. 1C. These internal threads 33 engage external threads 42 located on the forward end of a generally hollow herb chamber 40. External threads 44 on a rearward end of the herb chamber attach to internal threads 24 on a forward end of the cylindrical body 20. See FIG. 1B. In the present embodiment, when the mouthpiece 30 is in threaded engagement with the herb chamber 40, the cylindrical section 32 of the mouthpiece 30 extends over the herb chamber 40 and abuts with the forward end of the cylindrical body 10. See FIG. 1A.

Referring again to FIGS. 1B and 1C, a rearward interior portion of the herb chamber 40 houses a heating element 100, when the vaporizer 10 is assembled. A forward portion of the herb chamber 40 (i.e., in front of the heating element) provides an open internal space for placement of herbs. The heating element 100 is a convective heating element which heats air drawn into the herb chamber 40 from the air inlet apertures 22 in the cylindrical body. As illustrated, a screen 38 may be disposed within the mouthpiece 30 to prevent any particulate from passing through the device. In a further embodiment another screen (not shown) may be disposed within the herb chamber 40 proximate to the heating element 100.

An air nozzle 50 is positioned against a rearward end of the heating element 100 as best shown in FIG. 1C. The nozzle 50 extends from a small inlet aperture 51 (See FIG. 1C) to a larger exit aperture 52 (see FIG. 1B), juxtaposed against the rearward end of the heating element 100 to fluidly connect the inlet apertures 22 to the heating element 100, when the herb chamber 40 is in threaded connection with the cylindrical body 20. In the present embodiment, external threads 54 on a rearward end of the air nozzle 52 connect with internal threads of a mount 60 having a flange 64 received within the rearward end of the herb chamber 40. When assembled, the herb chamber 40 compresses a rim 66 of the mount 60 between against the bottom of the internal threads 24 of the forward end of the cylindrical body 10. A rearward surface of the mount 60 supports a forward electronics control circuit or forward circuit board 70. Connecting wires 150 (e.g., power wires, sensor wires etc.) of the heating element 100 pass through the air nozzle 50 for connection with the forward circuit board 70. Other connections are possible.

Figure 1D:
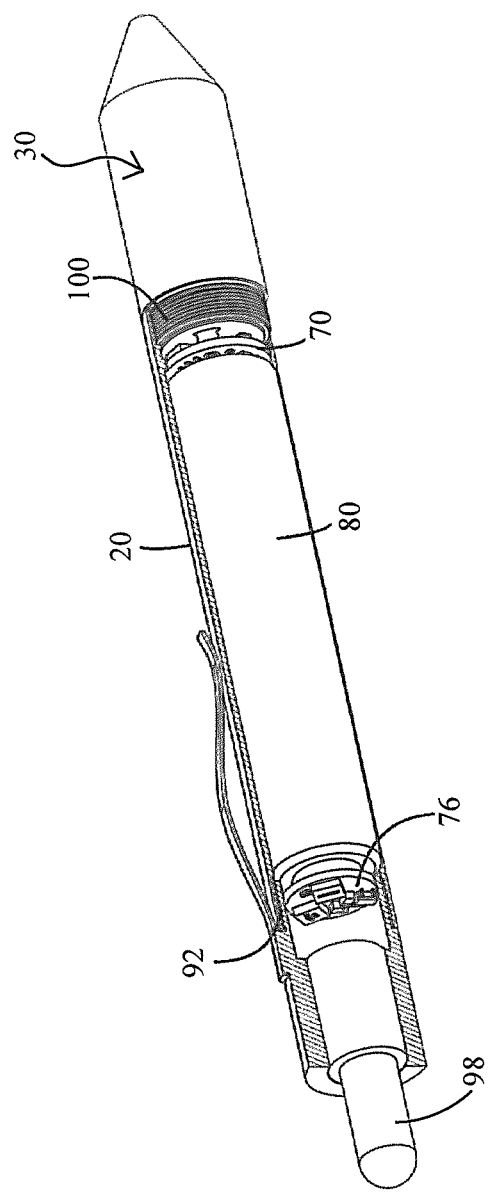
FIG. 1D is cross-sectional perspective view of a rearward portion of the vaporizer of FIG. 1A.

The cylindrical body 20 houses a battery 80 in its rearward portion behind the air inlet apertures 22. See FIG. 1B. An end cap assembly 90 having external threads 92 engages internal threads (not shown) on a rearward portion of the cylindrical body 20. When the end cap assembly 90 is in threaded engagement with the cylindrical body 20, a forward terminal of the battery 80 engages a first electrical contact 82 of the forward circuit board 70 and a second contact 94 of the end cap assembly 90 engages a rearward terminal of the battery 80. The end cap assembly 90 includes a power button 96 that allows for activating and deactivating the device 10 (i.e., completing an electrical circuit). Additionally, the end cap assembly 90 further includes a temperature adjustment dial 98, which allows for adjusting the temperature of air passing through the device. In one embodiment, the end cap assembly 90 further includes a rearward circuit board 76 which cooperates with the forward circuit board 70 to control the operation of the vaporizer 10. See FIG. 1D.

In use, a user removes the mouthpiece 30 from the herb chamber 40. Herbs are then placed within the forward portion of the herb chamber 40 in front of the heating element 100. At this time, a user may select a temperature setting using the temperature adjustment dial 98 and press the power button 96. The control circuitry then supplies electrical power to the heating element 100. Once the heating element achieves a desired temperature an indicator light (not shown) is illuminated to indicate that the vaporizer is ready for use. At this time, the user may draw air through the opening 36 in the mouthpiece, which draws air through the inlet apertures 22, through the nozzle 50, through the heating element 100 and through herbs within the herb chamber 40. The user receives vapors through the opening 36.

Figure 2:
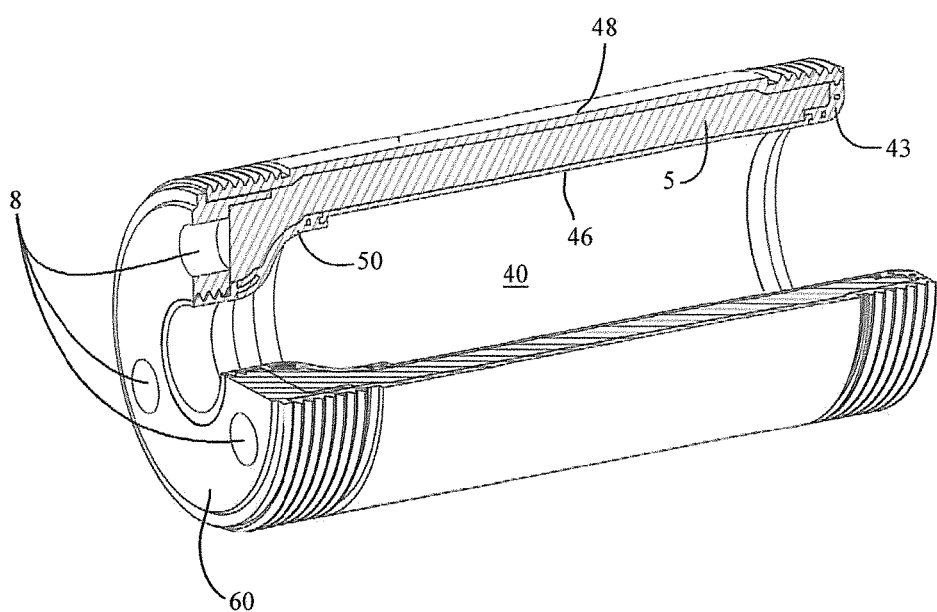
FIG. 2 is a cut away view of an herb chamber of the vaporizer of FIG. 1A.

FIG. 2 illustrates a cut away view of the herb chamber 40. As shown, the herb chamber is a double walled chamber having an internal housing 46 and an external housing 48. The internal housing 46 has a smaller diameter than the external housing 48 to define a void or insulation cavity/chamber 5 there between. The internal housing 46 is rigidly attached at a distal end to the external housing 48 using, in this example, a high-temperature polymer bracket 43. This forward annular bracket 43 forms a forward closed end of the insulation chamber 5. The proximal end of the internal housing 46 is connected to the external housing 48 by the nozzle 50 and mount 60. In such an arrangement, the nozzle 50 is essentially a rearward annular bracket that connects the housings via the mounting plate 60. The housings 46, 48, brackets 43, 50 and mounting plate 60 collectively define the insulation chamber 5. In the current embodiment, the brackets are injection over-molded onto the housings.

The void of the chamber 5 helps to thermally isolate the exterior of the herb chamber from the heated air within the chamber. Along these lines, it is noted that the temperatures required for vaporization (e.g., 350 to 400 degrees Fahrenheit) within the herb chamber could result in significant temperatures being applied to the external housing 48. To further reduce the transfer of thermal energy to the exterior housing 48, it is desirable to fill the chamber 5 with an insulating material. That is, the high vaporization temperatures within the herb chamber 40 require that a thermal barrier between the internal and external housing provide a temperature gradient that maintains the external surface temperature of the herb chamber 40 at a temperature that will not burn a user who touches this surface. The inventors have recognized that this gradient could be achieved by increasing the spacing between the internal housing and external housing and utilizing thicker insulation materials. However, this would undesirably increase the size of the vaporizer. Accordingly, the inventors have recognized it would be desirable to maintain a minimal spacing between the housings and instead utilize high-performance insulation. One particular high-performance insulation is Aerogel.

Aerogel is an ultralight porous material that is created from removing liquid from a gel material and replacing it with a gas through super critical drying. By removing the liquid through super critical drying, the remaining support matrix does not collapse as it would through a conventional drying process. The result is that Aerogels are good thermal insulators, which nearly nullify heat transfer by conduction and convection. Aerogel does not denote a specific material make up but instead a geometric structure. Silica aerogels were the first produced and still are the most used.

Silica aerogels are a precipitated silica composite, i.e., a composite formed from silicon and oxygen, with an extremely porous structure. Silica aerogels consist of a silica matrix that is approximately 96% air. More specifically, aerogels have continuous porosity, a cell or pore size less than 50 nm, surface area typically ranging between 400-1100 $m^2/g$, and a solid matrix composed of interconnected colloidal-like particles or fibrous chains with characteristic diameters of 10 nm. Silica aerogels typically have a thermal conductivity of 0.016 W/m*K under ambient conditions, much less than air, 0.026 W/m*K. In comparison to other insulators, aerogels offer a lower thermal conductivity especially considering how lightweight they are. Further, silica aerogels are non-flammable, nontoxic and thermally stable to about 650° C.

Aerogel can be fabricated into a number of forms including sheets, pellets and powders. Despite their exceptionally low thermal conductivity and weight, aerogels have not seen wide commercial use. Though monolithic, slab, aerogels are a candidate for many applications, the extensive and expensive processing equipment that is necessary for producing effectively sized aerogels is such that commercial use has been greatly limited. Using aerogel powders or microspheres, however, is a more economically viable alternative to slab aerogels. Aerogel particles have been used as loosely packed powders, an additive to applications such as paint, or creating composite insulation blankets.

One challenge of using aerogel particles is properly displacing such particles into an enclosed container (e.g., cavity). Aerogel particles are a form of material approaching dust. For instance, when a lid of a container of aerogel particles is removed, airflow caused by removing the lid displaces aerogel particles from within the container. As such, it is challenging to fill a cavity with a desired amount of aerogel particles to achieve a desired thermal conductivity level.

Prior attempts to fill cavities with aerogel particles have focused on using pressure and/or vacuum to control displacement of aerogel particles. One attempt to achieve proper packing of aerogel particles in a container is described in U.S. Pat. No. 6,598,283. Aerogel particles are sealed in a first container at a pressure less than atmospheric. When the pressure is reduced, the volume of the aerogel particles also drops. The first container is placed in a second container at a higher pressure and the first container, containing the aerogel particles, is breached causing normalization of pressure between the two containers. When this happens, the aerogel particles expand and fill the second container, as a result of the higher pressure. This method is limited however to the size of the second container. If the size of the second container is larger than the unrestrained volume of the aerogel particles at atmospheric pressure then undesirable shifting and settling will occur. Additionally, this method is not ideal because it requires multiple containers. In applications where space is an issue, as described above, aerogel may be selected because it is considered a super insulator and allows for the insulating layer to be thinner than other materials.

A second method for filling a cavity with aerogel particles, as described in U.S. Pat. App. No. 60/308,629 is by fluidizing aerogel particles with dry gaseous nitrogen and subjecting the aerogel particles to a slight positive pressure. A vacuum is simultaneously pulled on the cavity through a filter resulting in the aerogel particles filling the space. Then the cavity is evacuated with a vacuum pump leaving the aerogel particles behind. Though this can be an effective way to fill a space with aerogel particles, it is more complicated and costly than is necessary. Additionally, aerogel particles tend to clog the filters required in the process.

Figure 3:
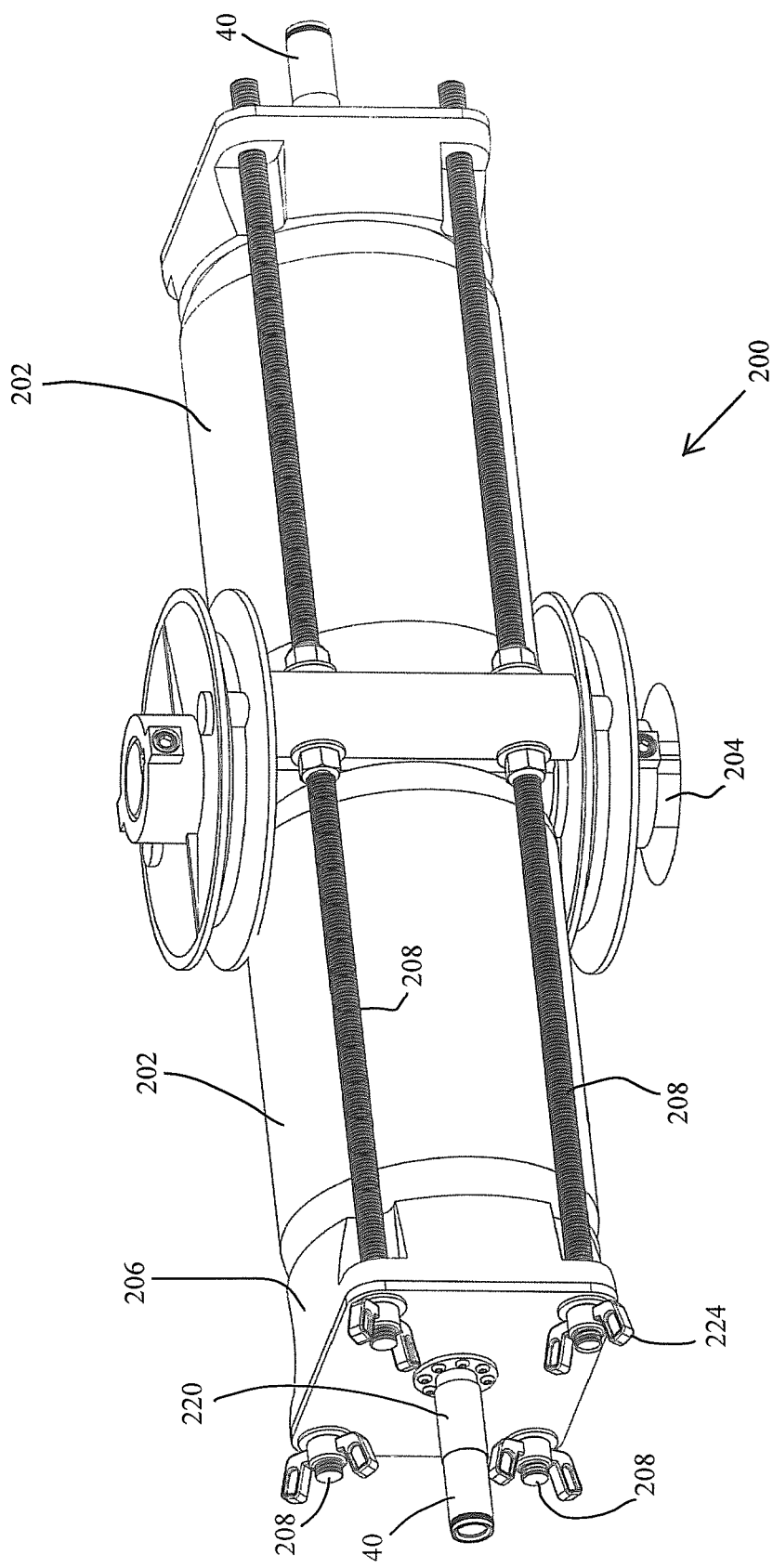
FIG. 3 illustrates a centrifuge assembly.

Instead of the above methods, the presented methodology utilizes centrifugal force to controllably fill a cavity with aerogel particles. Specifically, the inventors have recognized that use of a centrifuge allows controlling the flow and density of Aerogel particles into a cavity. FIG. 3 illustrates one embodiment of a centrifuge assembly 200, which may be utilized to controllably fill close-ended chambers or cavities with aerogel particles. As shown, the centrifuge assembly 200 includes a central shaft 204 about which the device rotates. A motor (not shown) is operative to control the rotation of the shaft 204. In the present embodiment, the centrifuge assembly 200 is adapted to support first and second aerogel wells 202 on opposing sides of the rotational shaft 204. Such an arrangement allows for balancing the centrifuge assembly 200. However, it will be appreciated that other configurations are possible and within the scope of the presented inventions.

The aerogel wells 202 are each affixed to the illustrated centrifuge assembly utilizing four threaded rods 208. The base of each rod 208 is connected to a support 212 proximate to the rotational shaft 204. Each set of four threaded rods 208 are evenly spaced around the periphery of the aerogel wells 202, which in the present embodiment are bottles of aerogel material. In order to attach to the aerogel bottles, a mounting body 206 includes internal threads 252 on its inward surface, which mate with external threads 250 of the aerogel bottle. See FIG. 4. In this regard, the mounting body 206 forms a cap of the bottle. Once the aerogel bottle is attached to the mounting body 206, the aerogel well 202 is disposed with the periphery defined by the four threaded rods 208 and free ends of the rods 208 extend through the corners of the mounting body 206. At this time, the mounting body is secured utilizing threaded fasteners such as wing nuts. When the threaded fasteners are tightened, the bottom or inward end of the aerogel well is disposed proximate to or against the shaft of the centrifuge assembly 200 and the aerogel well is fixedly supported relative to the shaft. As will be appreciated, when the centrifuge rotates around the shaft 204, aerogel material within the aerogel wells 202 is propelled outward due to centrifugal forces.

In order to transfer the aerogel from within the aerogel well 202 to an element having an internal chamber or cavity, this element must be attached to the centrifuge assembly outward of the aerogel well and be in fluid communication with the interior of the aerogel well. In the presented embodiment, the mounting body 206 further includes a mounting nozzle 220 that allows physically and fluidly connecting an element outward of the aerogel well.

Figure 4:
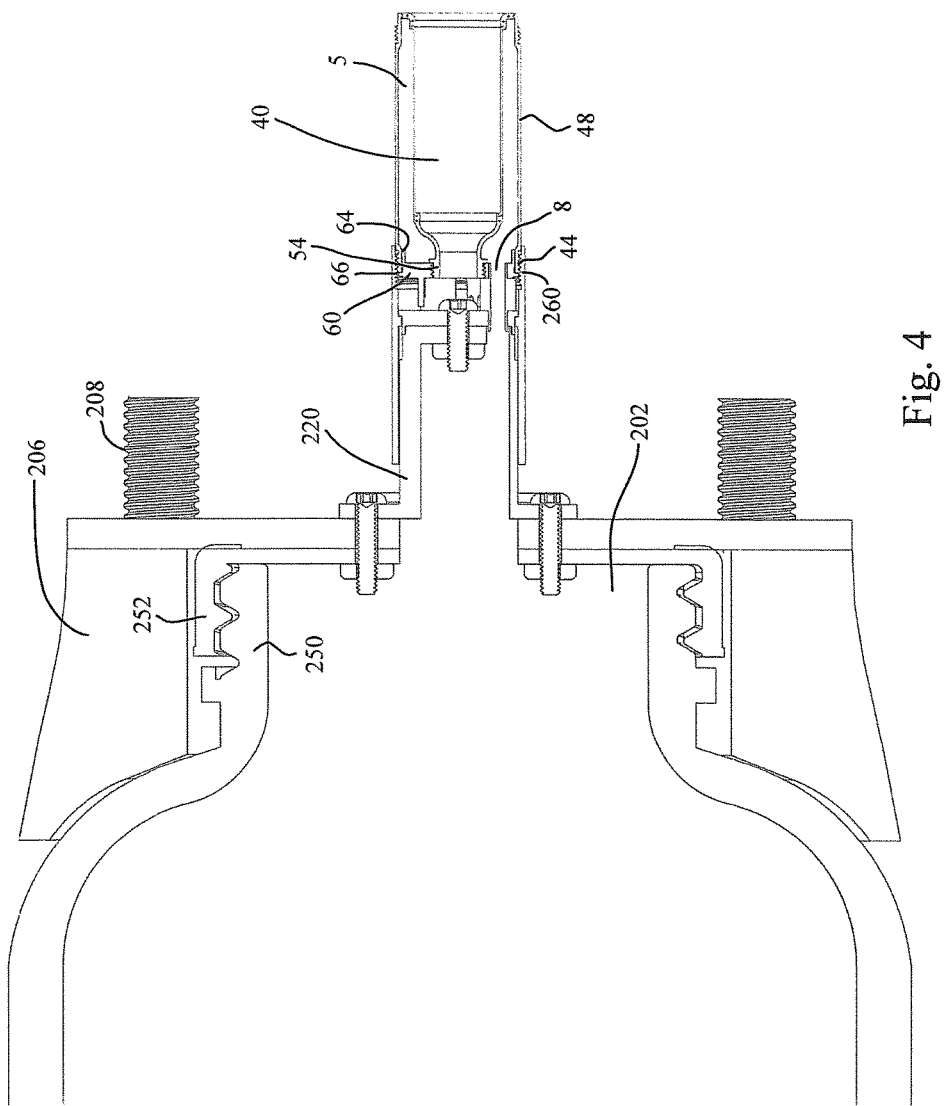
FIG. 4 is a cross-sectional perspective view of an aerogel well in fluid communication with a close-ended cavity.

FIGS. 3 and 4 illustrate the herb chamber 40 of the vaporizer described in relation to FIGS. 1A-1D as physically connected to the mounting nozzle 220 of the mounting body 206 such that it may receive aerogel particles from the interior of the aerogel well 202. More specifically, the rearward threaded end 44 of the herb chamber 40 engages with mating internal threads 260 of the mounting nozzle 220. As shown, the mounting nozzle 220 is a generally hollow tubular structure extending through the end surface of the mounting body 206 to provide a fluid channel between an attached element (e.g., herb chamber) and an interior of the aerogel well 202.

Referring again to FIG. 2, prior to assembly with the remainder of the vaporizer, the herb chamber 40 includes open fill holes 8 through the mount 60, which provide access to the cavity 5 between the internal and external housings. That is, the rearward end of the cavity 5 the herb chamber 40 is closed except for fill holes 8. As shown in FIG. 4, at least one of the fill holes 8 is aligned with the open interior of the mounting nozzle 220 when the herb chamber 40 is mounted to the centrifuge assembly. That is, the fill hole(s) 8 allow the herb chamber to be in fluid communication with the aerogel well 202 during the centrifuging process.

When the centrifuge is operated, centrifugal force causes the aerogel particles to migrate through fill holes 8 packing the herb chamber cavity 5 with aerogel particles. That is, by rotating the aerogel well 202 and cavity 40, the aerogel particles within the aerogel well 202 flow outward and migrate into the cavity 5 through at least one aperture 8 in the rearward end of the herb chamber 40. In one particular embodiment, fine aerogel particles having a particle size between 2-40 μm were utilized. Specifically, Enova® Aerogel IC3100 from Cabot Aerogel was utilized. When utilizing this material, test showed that rotation of a 280 mm radius centrifuge rotor at 3450 RPM (i.e., corresponding to a Relative Centrifugal Force (RCF) or G-force of approximately 3700) resulted in a compaction of the aerogel particles of approximately 8:1 compared to their original loose packing. Further RPM increases appear to show limited or no additional compaction. Further, compaction of nearly 7:1 was achieved at speeds of 2000 RPM (i.e., corresponding to a G-force of approximately 1250). It is believed that rotation of the aerogel well(s) 202 and chamber(s) 40 achieving RCFs of over 1000 will result in significant compaction of the aerogel particles. Along these lines, it is preferred that the aerogel particles be compacted in a ratio of at least 2:1 more preferably in a ratio of 6:1 and yet more preferably in a ratio of 8:1.

The high speed rotation of the aerogel particles results in a stratification of the particle air mixture and creates a compact mass of aerogel resembling a homogenous body. Once the insulation cavity 5 is filled, the herb chamber 40 is removed from the mounting nozzle 220. At this time, the fill apertures in the rearward end of the herb chamber may be sealed to maintain the aerogel particles within the insulation cavity 5. Any means of sealing the apertures may be utilized.

The cavity 5 may be entirely filled with an aerogel material. However, in further embodiments, the aerogel material may be admixed with additional components. For instance, carbon black particles (e.g., 30 micron particles) may be admixed with the aerogel material in the aerogel well. Such carbon enhances absorption of infrared radiation. As such, providing carbon black with the aerogel material may further improve the thermal gradient between the interior of the herb chamber and its exterior surface. In one embodiment, carbon black was mixed with aerogel in the aerogel well in a ratio of between 0.5% and 2.0% carbon to aerogel.

FIG. 5 illustrate a process for use in filling a cavity with aerogel particles. The process 300 include attaching 302 an aerogel well to a centrifuge device. Once the aerogel well is attached to the centrifuge device, an element having an internal cavity or chamber is attached 304 to the centrifuge device at a location outward (e.g., relative to a rotational axis) of the aerogel well. The internal cavity of the element is fluidly connected 306 to the interior of the aerogel well allowing for fluid communication of aerogel particles between the aerogel well and the internal cavity of the element. After these elements are attached and in fluid communication, the centrifuge device is rotated 308 to create centrifugal force resulting the aerogel particles transiting between aerogel well and the internal cavity of the attached element. Following rotation, the element may be removed and the cavity may be sealed to maintain the aerogel particles therein.

The foregoing description has been presented for purposes of illustration and description. Furthermore, the description is not intended to limit the inventions and/or aspects of the inventions to the forms disclosed herein. Consequently, variations and modifications commensurate with the above teachings, and skill and knowledge of the relevant art, are within the scope of the presented inventions. The embodiments described hereinabove are further intended to explain best modes known of practicing the inventions and to enable others skilled in the art to utilize the inventions in such, or other embodiments and with various modifications required by the particular application(s) or use(s) of the presented inventions. It is intended that the appended claims be construed to include alternative embodiments to the extent permitted by the prior art.

What is claimed is:

1. A method for filling a cavity with Aerogel particles, comprising:
   attaching an aerogel reservoir at least partially filled with aerogel particles to a centrifuge device at a first distance from a rotational axis of the centrifuge device;
   attaching an element having an internal cavity to the centrifuge device at a second distance from the rotational axis, wherein the second distance is greater than the first distance;
   fluidly connecting an interior of the aerogel reservoir with the internal cavity of the element; and
   rotating the aerogel reservoir and element about the rotational axis to migrate the aerogel particles from within the aerogel reservoir into the internal cavity of the element.

2. The method of claim 1, further comprising:
   rotating the aerogel reservoir and attached element to achieve a Relative Centrifugal Force (RCF) of at least 1000.

3. The method of claim 2, further comprising:
   rotating the aerogel reservoir and attached element to achieve a Relative Centrifugal Force (RCF) of at least 1250.

4. The method of claim 3, further comprising:
   rotating the aerogel reservoir and attached element to achieve a Relative Centrifugal Force (RCF) of at least 3000.

5. The method of claim 1, further comprising:
   admixing carbon black particles with the aerogel particles prior to rotation, wherein upon rotation, the carbon black particles migrate into the internal cavity of the element.

6. The method of claim 1, further comprising:
   removing the element from the centrifuge device and sealing the cavity.

* * * * *